United States Patent [19]
Aliotta et al.

[11] 3,997,329
[45] Dec. 14, 1976

[54] DENTAL COMPOSITION

[75] Inventors: Joseph Aliotta, Staten Island; Louis F. Alcuri, Brooklyn, both of N.Y.

[73] Assignee: Engelhard Minerals & Chemicals Corporation, Murray Hill, N.J.

[22] Filed: Dec. 29, 1975

[21] Appl. No.: 644,869

[52] U.S. Cl. .............................. 75/.5 R; 75/134 N; 75/169; 75/173 C
[51] Int. Cl.$^2$ ......................................... C22C 7/00
[58] Field of Search ............ 75/.5 R, 173 C, 173 R, 75/134 N, 134 C, 169

[56] References Cited
UNITED STATES PATENTS

| | | | |
|---|---|---|---|
| 1,963,085 | 6/1934 | Gray | 75/173 C |
| 2,281,991 | 5/1942 | Poetschke | 75/173 C |
| 3,305,356 | 2/1967 | Youdelis | 75/173 C X |
| 3,841,860 | 10/1974 | Wolf | 75/.5 R |
| 3,871,876 | 3/1975 | Asgar et al. | 75/169 |
| 3,933,961 | 1/1976 | Burns | 75/169 X |
| 3,954,457 | 5/1976 | Weikel | 75/169 |

*Primary Examiner*—L. Dewayne Rutledge
*Assistant Examiner*—E. L. Weise

[57] ABSTRACT

An improved dental composition comprises a uniform admixture in specified proportions of two powdered alloys of specified structure and composition, which when amalgamated with mercury produces a corrosion-resistant dental amalgam having enhanced mechanical properties and handling characteristics.

8 Claims, 3 Drawing Figures

DENTAL COMPOSITION

This invention relates to improved dental amalgam compositions and to their preparation. More specifically, it relates to a uniform admixture in designated proportions of two powdered alloys of specified composition and configuration, i.e., spheroids and irregularly-shaped particles which when amalgamated with mercury exhibits enhanced electrochemical and mechanical properties.

BACKGROUND

Dental amalgams are produced by intimately combining mercury with dental amalgam alloys, conventional of which are comprised generally of a major proportion of silver, a minor proportion of tin, and, optionally, copper and zinc in amounts usually substantially less than 10%. Upon reaction with mercury using known dental clinical techniques, a plastic mass is produced which quickly sets into a hard rigid body. While the mass is plastic, it may be packed into a surgically prepared tooth restoring its anatomy and function.

The products of the amalgamation reaction are believed to be a silver-mercury reaction product ($Ag_2Hg_3$) and a tin-mercury reaction product ($Sn_{7-8}Hg$), referred to in the art as gamma-1 and gamma-2, respectively. It has been recognized that the presence of gamma-2 in dental amalgams is a source of corrosion in a saline environment. It is believed that the corrosion process probably releases mercury as a reaction product, resulting in the formation of additional voids and porosities. These may extend well below the surface since the gamms-2 phase in dental amalgam is interconnected. The excess mercury, voids and porosities serve to weaken the dental amalgam especially at the margins which are the interfaces between the restoration and tooth. As a consequence of normal occlusion, stresses generated at a weakened margin may destroy its integrity, allowing leakage of oral fluids and bacteria, thereby promoting secondary decay.

Regardless of whether the aforementioned explanation of the corrosion process due to the presence of gamma-2 is correct (and the present invention is not necessarily limited thereto), it has been found that corrosion can be reduced by techniques which minimize, inhibit or eliminate gamma-2 from dental amalgam compositions. U.S. Pat. No. 3,305,356, for example, discloses the preparation of dental amalgams by mechanically dispersing a hard, strong metal alloy comprising copper and silver throughout a conventional amalgam in the form of very fine particles. There is evidence that in such compositions some of the copper from the dispersed silver-copper alloy combines with tin, thereby inhibiting gamma-2 formation. This is not effective immediately, however, since the copper must first diffuse through a reaction zone which forms around the dispersant. From a corrosion standpoint the gamma-2 is eliminated over a period of weeks after initial trituration and condensation.

Inhibition of gamma-2 has also been attempted by use of silver-tin alloys containing about 5% gold. While the formation of gamma-2 may be somewhat inhibited in such alloys, the resulting gold-tin phase that forms is also subject to saline corrosion. Moreover, the amount of gold required to eliminate gamma-2 completely makes such dental amalgams expensive.

Similarly, for a number of years some dentists have been adding empirical amounts of copper-mercury (copper amalgam) to already triturated conventional amalgam. This procedure produces a good clinical amalgam the structure of which appears to contain little or no gamma-2 phase immediately after trituration. The disadvantage of this technique is that the copper amalgam is heated until mercury beads at its surface prior to mixing. This presents a substantial mercury hazard to the dental personnel and perhaps to the patient.

Still other approaches have met with some success in minimizing or eliminating the gamma-2 phase, but with undesired side effects. For example, some otherwise successful compositions require increased amounts of mercury for amalgamation of the alloy.

Other approaches, which may employ high copper content compositions, are disclosed, for example, in U.S. Pat. Nos. 2,281,991 and 3,871,876. In the former a mixture of two comminuted alloys are employed, one, however, being a preformed hardened silver amalgam rich in silver and mercury, which requires special handling procedures. In the latter, advantageous results are reported for an amalgamable silver alloy powder, wherein each particle has a gradient composition from exterior to interior, a characteristic requiring special manufacturing techniques.

To achieve the required gradient composition of the aforesaid U.S. Pat. No. 3,871,876, the manufacturing techniques disclosed therein and in the prior art incorporated by reference therein, i.e., U.S. Pat. No. 3,253,783, provide particles which are generally spheroidal in configuration. An amalgam made from spheroidal powder, however, exhibits an undesirable feature. When the dentist attempts to pack it within a cavity, there is a tendency for the amalgam to ride up along walls of the cavity and to fail to pack as firmly as amalgams made from conventional irregularly-shaped microgranules, flakes or filings. It is to this latter problem that the present invention is primarily directed.

OBJECTS OF THE INVENTION

It is a general object of this invention to provide dental amalgam compositions which cope with the aforementioned problems of other amalgams.

It is a specific object to provide high-copper-content dental amalgamable compositions which are substantially free of mercury prior to amalgamation and which can be readily amalgamated without undue risks to personnel resulting from excessive mercury exposure.

It is another specific object to provide new dental amalgam compositions which upon amalgamation with mercury do not unduly form the gamma-2 phase and which provide enhanced physical, handling and electrochemical properties.

It is another specific object to provide dental amalgam compositions which upon amalgamation with mercury substantially immediately inhibit gamma-2 formation so as to be substantially free of the gamma-2 phase and yet are competitive in cost with other amalgam compositions.

It is another specific object to provide dental amalgam compositions having improved properties upon amalgamation without unduly increasing the amounts of mercury required in the preparation thereof.

It is another specific object to provide a dental amalgam composition having condensing, working, carving and adapting qualities superior to spheroidal amalgams or conventional irregularly-shaped microcut amalgams.

It is still another specific object to provide a dental amalgam which is substantially free of any tendency to ride up along walls of a cavity or to fail to pack as firmly as desired.

These and other objects will become apparent as the detailed description proceeds.

DESCRIPTION OF THE INVENTION

The new and improved dental amalgam composition of this invention comprises a uniform admixture of two alloy powders, hereinafter referred to as Alloy No. 1 and Alloy No. 2, respectively, the proportions and physical form of the two alloys being as set forth hereinafter.

Alloy No. 1 comprises spheroidal particles consisting essentially of the gradient composition from surface to core or center, as disclosed in the aforementioned U.S. Pat. No. 3,871,876, the disclosure being incorporated herein by reference, namely silver, tin and copper with silver present in the range of about 47% to 70% by weight, tin present in the range of about 20% to 32% by weight and copper present in the range of about 7% to 27% by weight, plus optional amounts of zinc up to about 2% by weight, these percentages generally corresponding to the composition ratios set forth in said patent. Alloy No. 2 comprises irregularly-shaped microgranules, flakes or filings consisting essentially of silver, tin and copper with silver present in the range of aout 40% to 70% by weight, tin in the range of about 10% to 30% by weight and copper in the range of about 20% to 40% by weight.

Alloy No. 1 is present as a major proportion of the powdered composition, i.e., more than about 50% by weight, e.g., about 55% to about 90% of the composition by weight, optimally about 70% to about 80%, whereas Alloy No. 2 is preferably present as a minor proportion, i.e., less than about 50% by weight, e.g., about 10% to about 45% by weight, optimally about 20% to about 30%. In an optimal case, the powdered alloys are present in the proportion of about 3 parts of Alloy No. 1 and about 1 part Alloy No. 2 by weight. Thus, for 100 parts of composition, approximately 75 parts of Alloy No. 1 are mixed with approximately 25 parts of Alloy No. 2.

The term "spheroidal" as used to describe the shape, configuration or form of the particulates of Alloy No. 1 in the admixture of the present invention means that the individual particles are spheres or shaped like a spheroid, that is, the particles are approximately spherical, and usually with a relatively smooth surface. A particle is approximately spherical if the largest dimension is no greater than about 130% of the smallest dimension. As aforementioned, processes for producing Alloy No. 1 in spheroidal form with the desired gradient composition are disclosed in U.S. Pat. No. 3,871,876. The term "spheroidal" will be more clearly understood from a consideration of the drawings hereinafter referenced.

The term "irregularly shaped" as used to describe the shape, configuration or form of the particulates of Alloy No. 2 means that the individual particles are substantially multi-sided and generally angularly shaped or rectilinear, albeit irregular, and usually with rough or otherwise relatively non-smooth surfaces. Typically they are in the form of what is variously referred to in the art as microcut material, lathe-cut material, platelets or filings. Conventional microcutting, lathe cutting or filing techniques can be employed satisfactorily to obtain the irregularly shaped particles and are well known to those skilled in the art. The term "irregularly shaped" will be more clearly understood from a consideration of said drawings hereinafter referenced.

The particle size distribution of both Alloy No. 1 and Alloy No. 2 is normally within the range of about 1 to about 100 microns, e.g., about 2 to about 80 microns, preferably about 5 to about 40 microns. The particle size range designation means that substantially all of the particles will pass a sieve or screen having openings corresponding to the larger size and substantially all of the particles will be retained on a sieve or screen having openings corresponding to the smaller size. The average particle size is typically in the range of about 20 to 30 microns, although the invention is not necessarily limited thereto.

To form a dental amalgam composition in accordance with this invention a major proportion of spheroids of Alloy No. 1 and a minor proportion of irregularly-shaped particulates of Alloy No. 2 are mechanically or manually mixed to produce a substantially uniform blend. In the preferred mechanical embodiment, the two alloys are mechanically mixed in a conventional blender for at least about 15 minutes, e.g., about ½ hour to about 1 ½ hours, typically about 1 hour. For dental use, the complete amalgam admixture is triturated with mercury in amounts of from about 0.8:1 up to about 1.5:1 parts of mercury by weight per part of the alloy powder. Preferably mercury is employed in a ratio of from about 0.9:1 to about 1.4:1 parts of mercury by weight per part of alloy powder, optimally a ratio of about 1:1.

Conventional trituration equipment and techniques may be employed, such as the condensation technique of the American Dental Association Specification No. 1 for dental amalgams. Typically, a one-spill trituration time of about 3–12 seconds at an amalgamator speed of about 3,000 to 5,000 revolutions per minute may be employed, e.g., a one-spill mixing time of about 5 seconds at about 3,500 revolutions per minute.

DESCRIPTION OF THE DRAWING

The present invention will be more clearly understood from the accompanying drawing wherein.

Figure 1:
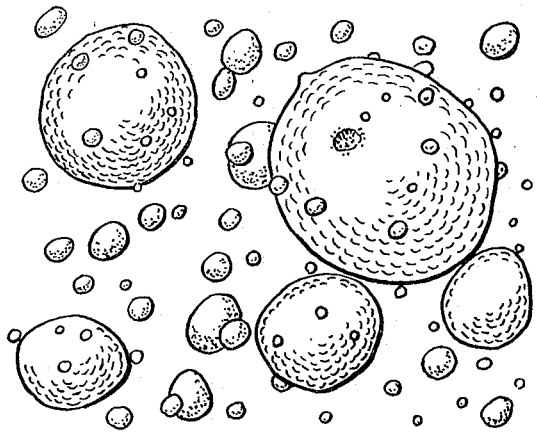
FIG. 1 is a highly magnified illustration of the spheroidal form of the particles of Alloy No. 1 which make up a major proportion of the blended dental amalgam of the present invention.
Figure 2:
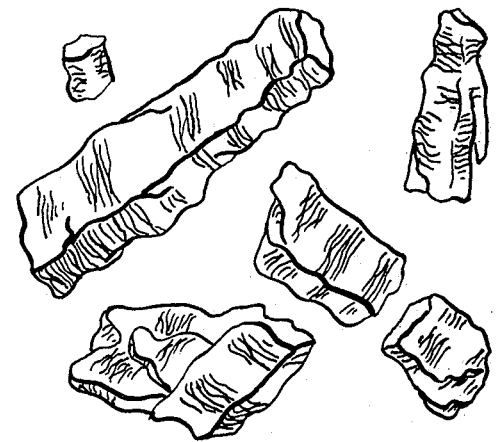
FIG. 2 is a highly magnified illustration of the irregularly-shaped form of the particles of Alloy No. 2 which make up a minor proportion of the blended dental amalgam of the present invention.
Figure 3:
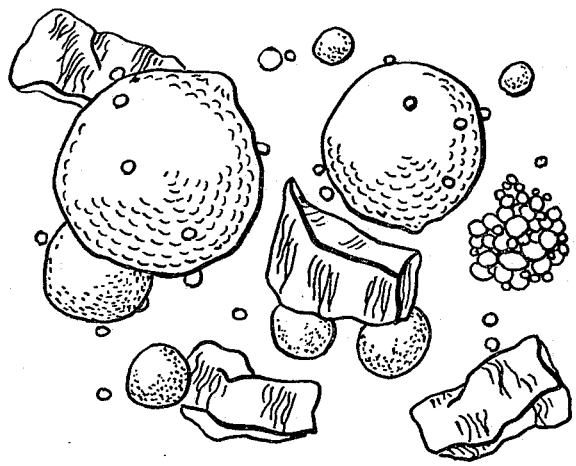
FIG. 3 is a highly magnified illustration of the blended dental amalgam of the present invention prepared by blending particles having the forms illustrated in FIGS. 1 and 2.

The following examples further illustrate the present invention and point up the advantages thereof.

EXAMPLE 1

The dental composition of the present invention was produced by mechanically mixing 3 parts by weight of an alloy containing 60% by weight silver, 27% by weight tin and 13% by weight copper in the form of spheriodal particulates having a gradient composition as disclosed in U.S. Pat. No. 3,871,876 and a particle size distribution in the range of about 1 to 100 microns, with 1 part by weight of an alloy containing 50% by weight silver, 20% by weight tin and 30% by weight copper in the form of flakes, also having a particle size distribution in the range of about 1 to 100 microns. Mechanical mixing of the two powdered alloys was employed to provide a substantially uniform blend. The resulting powdered dental composition was triturated in conventional manner with mercury using the condensation technique of the American Dental Association Specification No. 1 for dental amalgams, the weight ratio of mercury to composition being about 1:1.

The resulting dental amalgam was subjected to tests to determine physical characteristics, e.g., working time, diametral tensile strength, flow characteristics and dimensional change. The results were as follows:

| Working Time (Minutes) | 15-Minute Diametral Tensile Strength psi | One-Hour Diametral Tensile Strength, psi | Flow Test, % | 24-Hour Dimensional Change microns/cm |
|---|---|---|---|---|
| 6 | 400 | 6,000 | 0.05 | +5 |

The amalgam was checked for the presence of the gamma-2 phase. This was done by anodic polarization measurements in saline solution about 24 hours after trituration and condensation, the results being presented in the form of an anodic polarization diagram. Such technique and diagram represents one means of detecting the presence of gamma-2, the indication being a current density peak at about −250 mv(SCE), indicative of the formation of tin oxide or tin oxychloride. The technique is at least as sensitive as X-ray diffraction for the detection of gamma-2 and is further described in the literature, e.g., Journal of Dental Research, Vol. 51, No. 6, November-December 1972, at page 1675 (Copyright 1972 by International Association for Dental Research). The anodic polarization diagram for the amalgam of this example showed no substantial current density peak at −250 mv, indicating its resistance to gamma-2 corrosion. Further illustrative examples are as follows:

EXAMPLE 2

An amalgamable dental composition in accordance with the invention is prepared by mechanically mixing 4 parts of an alloy composed of 55% by weight silver, 28% by weight tin and 17% by weight copper in the form of spheroidal particulates having a gradient composition from surface to core as disclosed in U.S. Pat. No. 3,871,876, with 2 parts of an alloy composed of 55% by weight silver, 18% by weight tin, and 27% by weight copper in the form of irregularly-shaped flakes. Both powders have a particle size distribution within the range of about 2 to 80 microns.

EXAMPLE 3

An amalgamable dental composition in accordance with the invention is prepared by mechanically mixing 4 parts of an alloy composed of 65% by weight silver, 24% by weight tin and 16% by weight copper in the form of spheroidal particulates having a gradient composition from surface to core as disclosed in U.S. Pat. No. 3,871,876, with 1 part of an alloy composed of 45% by weight silver, 24% by weight tin, and 31% by weight copper in the form of irregularly-shaped flakes. Both powders have a particle size distribution within the range of about 2 to 80 microns.

EXAMPLE 4

An amalgamable dental composition in accordance with the invention is prepared by mechanically mixing 3 parts of an alloy composed of 58% by weight silver, 26% by weight tin and 16% by weight copper in the form of spheroidal particulates having a gradient composition from surface to core as disclosed in U.S. Pat. No. 3,871,876, with 2 parts of an alloy composed of 62% by weight silver, 14% by weight tin, and 24% by weight copper in the form of irregularly-shaped flakes. Both powders have a particle size distribution within the range of about 2 to 80 microns.

While it is essential that the dental composition of this invention be in the form of a mixture of particulates of the two alloys when used, and may be supplied in such form when supplied, it should be understood that for distribution purposes the two alloys can be in the form of separate powders which can be admixed by the ultimate user in the required proportions. Alternatively, the two admixed alloys in the required proportions can be pressed into tablet or capsule form for convenience.

While only certain embodiments have been set forth, alternative embodiments and various modifications of the embodiments depicted will be apparent from the above description to those skilled in the art. These and other alternatives are considered equivalents and within the spirit and scope of the present invention.

Having described the invention, what is claimed is:

1. A composition adapted for amalgamation with mercury to form a dental amalgam comprising a substantially uniform blend of:
    a. a major proportion by weight of a first alloy in the form of spheroidal particles having a particle size distribution in the range of about 1 to about 100 microns and consisting essentially of about 47% to 70% by weight silver, about 20% to 32% by weight tin, and about 7% to 27% by weight copper, each of the spheroidal particles of said first alloy having a gradient composition from the surface to the center thereof; and
    b. a minor proportion by weight of a second alloy in the form of irregularly-shaped particles having a particle size distribution in the range of about 1 to 100 microns and consisting essentially of about 40% to 70% by weight silver, about 10% to 30% by weight tin, and about 20% to 40% by weight copper.

2. The composition of claim 1 containing about 55% to about 90% by weight of said first alloy and about 10% to about 45% by weight of said second alloy.

3. The composition of claim 1 containing approximately 3 parts by weight of said first alloy and 1 part by weight of said second alloy.

4. The composition of claim 1 wherein said first alloy contains up to about 2% zinc.

5. The composition of claim 1 amalgamated with about 0.8 to 1.5 parts by weight of mercury per part of composition to form a workable dental amalgam.

6. A process for preparing a dental amalgam which comprises triturating the composition of claim 1 with sufficient mercury to form a workable plastic amalgam.

7. A composition adapted for amalgamation which mercury to form a dental amalgam comprising a substantially uniform blend of:

a. about 70% to about 80% by weight of a first alloy in the form of spheroidal particles having a particle size distribution in the range of about 2 to about 80 microns and consisting essentially of about 47% to 70% by weight silver, about 20% to 32% by weight tin, and about 7% to 27% by weight copper, each of the spheroidal particles of said first alloy having a gradient composition from the surface to the center thereof; and b. about 20% to about 30% by weight of a second alloy in the form of irregularly-shaped particles having a particle size distribution in the range of about 2 to 80 microns and consisting essentially of about 40% to 70% by weight silver, about 10% to 30% by weight tin, and about 20% to 40% by weight copper.

8. A process for preparing a dental amalgam which comprises triturating the composition of claim 7 with mercury in the proportion of about 0.8 to about 1.5 parts by weight of mercury per part by weight of said composition to form a workable plastic amalgam.

\* \* \* \* \*